United States Patent [19]

Johansson et al.

[11] Patent Number: 5,266,094
[45] Date of Patent: Nov. 30, 1993

[54] METHOD RELATING TO THE PRODUCTION OF AMORPHOUS TEST BODIES

[75] Inventors: Hi K. E. Johansson, Täby; Ann-Christine M. Jakobsson; Ove R. A. Lindmark, both of Ursviken; Karl J. Malmqvist, Byske, all of Sweden

[73] Assignee: Boliden Mineral AB, Skelleftehamn, Sweden

[21] Appl. No.: 880,035

[22] Filed: May 8, 1992

[30] Foreign Application Priority Data

May 30, 1991 [SE] Sweden .................................. 9101629

[51] Int. Cl.$^5$ ............................................. C03B 19/00
[52] U.S. Cl. .......................................... 65/66; 65/134; 73/864.91
[58] Field of Search .................. 65/66, 134; 73/864.91

[56] References Cited

U.S. PATENT DOCUMENTS 4,793,844 12/1988 Panayotov .......................... 65/134

FOREIGN PATENT DOCUMENTS 2240809 2/1974 Fed. Rep. of Germany.
1397849 6/1975 United Kingdom.

OTHER PUBLICATIONS

Derwent's Abstracts No. 90–43 411/06, SU 1,497,536, pub. week. 9006.
X-Ray Spectrometry, vol. 19, 1990, J. Eastell et al., "A Low Dilution Fusion Technique for the Analysis of Geological Samples", pp. 3–14,
X-Ray Spectrometry, vol. 19, 1990, K. Norish et al., "XRS Analysis of Sulphides by Fusion Methods", John Wiley & Sons, Ltd., pp. 67–71.

Primary Examiner—W. Gary Jones
Assistant Examiner—Steven P. Griffin
Attorney, Agent, or Firm—Burns, Doane, Swecker & Mathis

[57] ABSTRACT

A method of producing amorphous sample bodies which can be used for optical spectral analysis and X-ray spectral analysis, by fusing an analysis sample together with flux and by introducing finely-divided $SiO_2$ in a quantity corresponding to from 1–100% of the sample quantity, prior to the fusion process. Sample bodies obtained when practicing the inventive method are used for the analysis of geological material, inorganic environmental sample material and sulfidic and/or oxidic products obtained from ferrous and non-ferrous manufacturing processes.

12 Claims, No Drawings

METHOD RELATING TO THE PRODUCTION OF AMORPHOUS TEST BODIES

The present invention relates to a method relating to the production of amorphous test bodies for use in optical spectral analysis and X-ray spectral analysis, by fusing a sample intended for analysis together with a flux.

A great deal of work has been undertaken in recent decennia in developing methods for the production of sample bodies for analysis. This has been necessary because all types of analysis activity requires the analysis sample, or test piece, to be as homogenous as possible. A well-produced, amorphous glass has this property. In the case of X-ray spectral analysis, it is, for instance, difficult to obtain by mechanical machining processes (fine grinding) a homogeneity or particle size which will not have a disturbing effect on the subsequent analysis. Optical spectral analysis normally requires the use of solutions which are devoid of not-readily dissolved solid particles. Consequently, attempts have been made to develop more sophisticated fusion methods for the production or manufacture of amorphous test bodies. Such fusion methods are generally based on mixing the analysis sample with a flux and then fusing the flux-sample mixture and moulding a glass brick or briquette in an appropriate shape. The flux used is primarily a borate chosen from among a number of different borates, for instance lithium tetraborate, although other fluxes are mentioned in the literature, such as lanthanum oxide, lithium metaborate, etc. This method of preparing sample bodies for optical and X-ray analysis are today considered to provide such good results that each sample material which will dissolve in a borate glass produced with the aforesaid conventional fluxes is now analyzed spectral analytically. In the case of many materials, for instance materials which contain large quantities of basic oxides, sulfides or metals, difficulties occur in the preparation of homogenous sample bodies. In such cases, crystalline formations frequently occur, which in practice renders the analysis of such sample bodies impossible for many types of inorganic material, for instance geological samples, environmental samples, sulfidic and/or oxidic products containing different intermediate products from ferrous and non-ferrous manufacturing processes.

One of the latest proposed sample preparing methods for the analysis of geological samples, the so-called LDF-method (Low Dilution Fusion) is described in an article published in X-Ray Spectrometry, vol. 19, pages 3–14 (1990). The method was developed for the purpose of solving the sample preparation problems that are encountered with particularly troublesome types of rock and minerals, for instance lamproites and kimberlites, these minerals having been formed under high pressures and high temperatures. The flux used is a mixture of 20% lithium tetraborate and 80% lithium metaborate, and an oxidation agent is added, for example an oxidation agent from the group $NH_4NO_3$, $LiNO_3$ and $NaNO_3$. The oxidation of oxidizable constituents takes place during fusion of the sample-flux-mixture.

A fusion method which has long been used at Mount Isa Mines for preparing geological samples and different products from smelting plants is described in X-Ray Spectrometry, vol. 19, pages 67–71 (1990). This fusion method enables sulfidic samples to be prepared by employing pre-oxidation with sodium nitrate at 700° C. over a short period. Other additives include a conventional flux which consists of different lithium borates.

Thus, many materials which are relevant for analysis at laboratories which are connected to mines and smelting plants will include such high concentrations of sulphur and/or heavy metals as to render it necessary to analyze said materials by other methods, since hitherto it has not been possible to produce sample bodies of sufficient homogeneity. For example, it can be mentioned that when experimenting with the LDF-method in our analysis laboratory at the smelting plant in Rönnske,uml/a/ r (Sweden), samples of different types of copper matte, white metal (i.e. concentrated copper matte) and oxide products having high zinc concentrations were found to indicate several crystalline phases during the X-ray diffraction process.

Consequently, there is a need to further develop the sample preparing methods in order to enable amorphous, homogenous sample bodies to be produced from all of the materials which may be presented for analysis in, for instance, the laboratory of a smelting plant. Naturally, the prime reason for this is because analysis costs must be kept at a low level, for instance by rationalizing sample preparation processes, so as to enable all materials relevant for analysis to be prepared in one and the same way and preferably in solely one single sample preparation. It is not possible to accept a reduction in the accuracy of the analyses, and consequently particularly high demands must be placed on the sample preparation method and these demands must be particularly specific.

It has now been found surprisingly possible to provide a method of preparing samples in the aforedescribed manner with the purpose of fulfilling the requirements or demands discussed above. The object of the invention is to avoid all crystalline formations in the sample bodies and to enable all types of inorganic geological material, inorganic environmental sample material, and sulfidic and/or oxidic products, including various intermediate products deriving from ferrous and non-ferrous manufacturing processes to be analyzed. This object is achieved by the inventive method having the characteristic features set forth in the following claims.

Thus, according to the present invention, finely-divided $SiO_2$ is added to the sample in an amount corresponding to 1–100% of the sample quantity prior to the fusion process, in addition to a conventional flux. By "finely-divided $SiO_2$" is meant any form of silica which is so finely divided as to be readily mixed intimately with sample and flux when weighing the sample mixture to be fused. Preferably, however, chemically pure $SiO_2$ products of the kind available for laboratory purposes are used.

If the sample is of a type which is judged to contain sulphur in concentrations higher than 1–2% and/or other oxidizable elements, a predetermined quantity of suitable oxidation agent is also added to the sample mixture, so as to oxidize the sulphur and the other oxidizable elements. In this regard, the oxidation agent is normally added in an amount which corresponds to about 50% of the sample quantity in the case of sulphur concentrations of up to about 10%, and in quantities above 50% at higher sulphur concentrations.

Oxidation of the sample can also be effected with or without the addition of an oxidation agent, by subjecting the sample to an oxidizing process at elevated temperature, prior to fusing the sample together with its additives. The oxidation agent used is suitably lithium nitrate. Fusion of the sample mixture is preferably carried out in a platina crucible, by placing the crucible in a electrical resistance furnace set to a temperature of about 1200° C. An advantage is gained when the fusion process is divided into two five-minute periods, between which the crucible is removed and the sample stirred or agitated, for instance by gently rotating the crucible in a circular fashion.

Upon completion of the fusion process, the molten material is poured directly into a chilled crucible or into suitable moulds adapted for the X-ray equipment concerned, i.e. ED-(energy dispersive) or WD-(wavelength dispersive) X-ray equipment.

The invention also relates to the use of the amorphous sample bodies produced for the analysis of geological material and sulfidic and/or oxidic products, and also different intermediate products deriving from the ferrous and non-ferrous manufacturing processes.

Table 1 below illustrates typical concentration ranges for elements that can be analyzed by means of the inventive method and with the aid of an X-ray analyzing system, Philips PW/1610.

TABLE 1

| Element | Dynamic Concentration Range % | Element | % |
|---|---|---|---|
| $Na_2O$ | 0.05–10 | $K_2O$ | 0.01–20 |
| MgO | 0.05–100 | CaO | 0.01–100 |
| $Al_2O_3$ | 0.05–100 | $TiO_2$ | 0.002–5 |
| SiO | 0.05–100 | Cr | 0.002–5 |
| S | 0.01–30 | MnO | 0.002–5 |
| $Fe_2O_3$ | 0.01–100 | As | 0.002–25 |
| Co | 0.001–5 | BaO | 0.01–5 |
| Ni | 0.001–30 | Pb | 0.005–70 |
| Cu | 0.001–70 | Sr | 0.0005–1 |
| Zn | 0.001–70 | Mo | 0.0005–1 |
| Ag Cd Sn Sb Bi | 0.001–10 | | |

The invention will now be described in more detail with reference to exemplifying embodiments thereof and also with reference to analyses carried out to international standards.

Described below is a preferred method of preparing the sample.

The sample is weighed in a finely-divided state in platina crucibles, for instance 30 ml crucibles Pt/Au 90:10 (Johnson & Matthey). A suitable sample/additive ratio is:

1.00 g sample
4.75 g flux (e.g. Spectroflux 100 B)
0.25 g silica (annealed at 1150° C.)

Preferably, the weighing process is started with flux in platina crucibles directly on the scales, whereafter the remaining components are added in a conventional manner. Flux and silica can be weighed beforehand. If an oxidation agent is to be added, this is done in accordance with one of the following alternatives, which have been found to provide a good oxidation result with the lowest possible losses.

| | | |
|---|---|---|
| Ore and rock | 0.50 g $LiNo_3$ | Merck Suprapur |
| Remainder (S < 10%) | 1.00 g $LiNO_3$ | Fischer Scientific Comp |
| Remainder (S > 10%) | 2.00 g $LiNO_3$ | Fischer or Merck |

The oxidizing treatment was carried out from a cold furnace up to a furnace temperature of about 700° C. over a period of up to 3 hours.

The crucible was then placed in the melting furnace, which was adjusted to a temperature of about 1200° C. for 5 minutes, whereafter the crucible was removed, gently shaken and then returned to the furnace for a further 5 minutes. These time periods were measured with a signal clock. The molten material was then poured into an appropriate, chilled mould which accommodated precisely the quantity of molten material in the crucible. The amount of silica added to the sample mixture shall be adapted to the different types of material to be analyzed. It has been found that a silica addition which is less than 1% of the sample quantity is not sufficient to glassify basic oxides for instance. Completely amorphous sample bodies can thereafter be obtained with increasing additions of silica. When the produced sample body contains silica in excess of about 100% of the sample quantity, however, the sample body is no longer of such interest from an analytical aspect. The addition of silica must therefore constitute a well-balanced compromise, since the possibility of analyzing $SiO_2$ in an optimum fashion will otherwise be lost. When used in practical applications of analyses with silica additions balanced in accordance with the invention, the invention will provide good results also with respect to $SiO_2$.

EXAMPLE 1

Amorphous sample bodies were manufactured in accordance with the invention to a large number of international analysis standards. The sample bodies were then analyzed in X-ray spectral equipment of the type PW 1600 having 28 channels. The sample bodies were evaluated conventionally with a so-called fundamental evaluation model, resulting in the analyses set forth in Table 2. The left-hand column of the Table contains the designations for the various standard samples, the "certified" composition being given uppermost for each sample and the contents or concentrations analyzed by the method are given beneath respective elements. It can be said that satisfactory agreement was reached both with higher concentrations and with concentrations in the trace substance range.

TABLE 2

An Analysis of International Analysis Standards

| | | Na₂O % | MgO % | Al₂O₃ % | SiO₂ % | S % | K₂O % | CaO % | TiO₂ % | Cr % | Mn % | Fe₂O₃ % | Co % | Ni % | Cu % | Zn % | As % | Sr % | Mo % | BaO % | Pb % |
|---|---|---|---|---|---|---|---|---|---|---|---|---|---|---|---|---|---|---|---|---|---|
| 1 | AKR | .08 | .19 | .19 | 1.13 | .08 | .06 | 96.77 | .007 | .0003 | .006 | .23 | .0002 | | .0008 | .0036 | .002 | .4174 | | .006 | .0053 |
| 2 | AKR | .02 | .14 | .17 | 1.13 | .10 | .05 | 95.70 | .007 | .0001 | .005 | .22 | .0000 | | .0004 | .0026 | .004 | .4547 | .0000 | .003 | .0065 |
| 3 | ASKI | 6.50 | 1.10 | 18.60 | 59.50 | .06 | 4.50 | 3.20 | 1.168 | .0050 | .142 | 4.60 | .0000 | .0120 | .0007 | .0076 | .001 | .0680 | .0005 | .126 | .0006 |
| 4 | ASKI | 6.23 | 1.10 | 18.43 | 59.65 | .06 | 4.18 | 3.53 | 1.064 | .0030 | .144 | 4.75 | .0000 | .0129 | .0011 | .0113 | .001 | .0690 | .0000 | .122 | .0002 |
| 5 | BCS267 | .06 | .06 | .85 | 95.90 | | .14 | 1.75 | .170 | | .150 | .79 | | | | | | | | | |
| 6 | BCS267 | .05 | .07 | .87 | 96.99 | .03 | .13 | 1.74 | .169 | .0115 | .158 | .77 | .0003 | .0019 | .0089 | .0007 | .002 | .0013 | .0018 | .012 | .0012 |
| 7 | CCU1 | | | .25 | 2.61 | 35.40 | | | | | | 44.14 | | | 24.7100 | 3.2200 | | | | | .1060 |
| 8 | CCU12 | .26 | 1.27 | .21 | 2.61 | 35.33 | .01 | .09 | .020 | .0007 | .020 | 43.70 | .0067 | .0201 | 24.7136 | 3.2104 | .004 | .0007 | .0044 | .030 | .1065 |
| 9 | CZN1 | | | .25 | | 30.20 | | | | | .219 | 15.63 | | | .144044 | .7600 | | | | .0007 | .6500 |
| 10 | CZN12 | .33 | .71 | .23 | .84 | 29.39 | .03 | .26 | .034 | .0007 | .225 | 15.20 | .0092 | .0266 | .150345 | .1800 | .005 | .0167 | .0091 | .0007 | .6100 |
| 11 | ER1 | .03 | .30 | .52 | 16.95 | .26 | .02 | 3.29 | .030 | .0007 | .220 | 75.86 | .0012 | .0008 | .0100 | .3500 | .026 | .0090 | | .112 | .5200 |
| 12 | ER1 | .04 | .40 | .46 | 16.37 | .27 | .02 | 3.24 | .029 | .0033 | .229 | 76.86 | .0000 | .0015 | .0097 | .3617 | .029 | .0096 | .0028 | .113 | .5385 |
| 13 | ER4 | .04 | 1.41 | 1.70 | 50.07 | .11 | .29 | 2.23 | .070 | .0009 | .190 | 39.92 | .0002 | .0006 | .0013 | .0027 | .001 | .0062 | | .005 | .0008 |
| 14 | ER4 | .05 | 1.35 | 1.64 | 49.96 | .15 | .28 | 2.26 | .065 | .0023 | .204 | 39.92 | .0005 | .0000 | .0006 | .0019 | .001 | .0042 | .0000 | .003 | .0034 |
| 15 | ES8771 | .31 | .47 | .08 | 2.32 | .18 | .07 | 4.52 | .053 | .0173 | 1.774 | 88.75 | | .0097 | .0006 | | .014 | | | | .9989 |
| 16 | ES8771 | .35 | .53 | .06 | 2.60 | .20 | .06 | 4.55 | .058 | .0191 | 1.798 | 88.26 | .0011 | .0100 | .0269 | 1.1600 | .017 | .0059 | .0043 | .0081 | .0227 |
| 17 | MKR | .05 | 88.95 | .81 | 1.17 | .01 | .03 | 1.14 | .037 | .0013 | .315 | 6.79 | .0002 | .0010 | .0267 | 1.1803 | | .0012 | | .006 | .0003 |
| 18 | MKR | .04 | 88.01 | .82 | 1.08 | .02 | .01 | 1.25 | .032 | .0022 | .327 | 6.98 | .0022 | .0023 | .0005 | .0030 | .001 | .0011 | .0000 | .010 | .0011 |
| 19 | MRG1 | .71 | 13.69 | 8.50 | 39.32 | .06 | .18 | 14.77 | 3.690 | .0450 | .170 | 17.82 | .0086 | .0195 | .0135 | .0018 | .000 | .0260 | .0000 | .005 | .0010 |
| 20 | MRG1 | .78 | 13.71 | 8.34 | 39.88 | .08 | .19 | 15.13 | 3.766 | .0456 | .183 | 18.28 | .0081 | .0206 | .0142 | .0190 | .004 | .0257 | .0029 | .010 | .0023 |
| 21 | NBS1633A | .23 | .75 | 26.45 | 48.77 | | 2.26 | 1.55 | 1.384 | .0196 | .026 | 13.44 | .0046 | .0127 | .0118 | .0230 | .015 | .0830 | .0027 | .167 | |
| 22 | NBS1633A | .22 | .77 | 27.16 | 49.43 | .21 | 2.29 | 1.65 | 1.381 | .0171 | .034 | 13.64 | .0042 | .0136 | .0143 | .0252 | .012 | .0812 | | .164 | .0084 |
| 23 | NBS78A | .08 | .70 | 71.70 | 19.40 | | 1.22 | .11 | 3.200 | | | 1.20 | | | | | | .2114 | | | |
| 24 | NBS78A | .14 | .74 | 71.77 | 19.85 | .03 | 1.27 | .13 | 3.210 | .299 | .017 | 1.27 | .0000 | .0057 | .0109 | .0029 | .003 | .2160 | .0032 | .078 | .0091 |
| 25 | NBS97A | .04 | .15 | 38.79 | 43.67 | | .50 | .10 | 1.900 | .0200 | .011 | .45 | .0002 | .0103 | .0073 | .0046 | .007 | .1522 | .0015 | .075 | .1819 |
| 26 | NBS97A | .02 | .23 | 39.14 | 44.18 | .07 | .56 | .11 | 1.897 | .0227 | .021 | .46 | .0004 | .0008 | .0012 | .0050 | .002 | .1502 | .0003 | .085 | .0040 |
| 27 | SARM1 | 3.36 | .06 | 12.08 | 75.70 | .01 | 4.99 | .78 | .090 | .0012 | .019 | 2.02 | .0003 | .0015 | .0000 | .0064 | .004 | .0010 | .0005 | .013 | .0036 |
| 28 | SARM1 | 3.36 | .05 | 12.16 | 76.29 | .01 | 5.06 | .81 | .079 | .0005 | .001 | 1.99 | .0003 | .0007 | .0019 | .0113 | | .0003 | | .005 | .0005 |
| 29 | SARM2 | .43 | .46 | 17.34 | 63.63 | .02 | 5.35 | .68 | .044 | .0012 | .001 | 1.40 | .0002 | .0020 | .0016 | .0010 | .005 | .0062 | .0000 | .262 | .0007 |
| 30 | SARM2 | .54 | .47 | 17.33 | 64.01 | .07 | 15.49 | .69 | .039 | .0018 | .001 | 1.41 | .0002 | .0020 | .0014 | .0016 | .002 | .0052 | .0005 | .273 | .0012 |
| 31 | SARM4 | 2.46 | 7.50 | 16.50 | 52.64 | | .25 | 11.50 | .200 | .0030 | .180 | 8.91 | .0058 | .0120 | .0011 | .0068 | .000 | .0260 | .0000 | .011 | .0031 |
| 32 | SARM4 | 2.48 | 7.67 | 16.57 | 53.14 | | .25 | 12.09 | .183 | .0047 | .193 | 9.24 | .0058 | .0136 | .0018 | .0067 | .005 | .0245 | .0005 | .000 | .0006 |
| 33 | SARM5 | .37 | 25.33 | 4.18 | 51.10 | .06 | .09 | 2.66 | .200 | 2.4000 | .220 | 12.76 | .0110 | .0555 | .0015 | .0100 | .005 | .0032 | .0000 | .005 | .0041 |
| 34 | SARM5 | .37 | 25.81 | 4.15 | 51.40 | | .08 | 2.76 | .180 | 2.4113 | .241 | 13.00 | .0105 | .0583 | .0015 | .0113 | | .0009 | .0000 | .004 | .0007 |
| 35 | SARM6 | .04 | 43.51 | .30 | 38.96 | .01 | .01 | .28 | .020 | 2.9000 | .220 | 16.96 | .0208 | .2050 | .0010 | .0090 | | .0003 | .0004 | .001 | .0039 |
| 36 | SARM6 | .17 | 43.38 | .26 | 39.19 | .02 | .01 | 2.9 | .011 | 2.8905 | .232 | 17.27 | .0203 | .2078 | .0006 | .0096 | .005 | .0025 | .0001 | .000 | .0039 |
| 37 | SY2 | 4.34 | 2.70 | 12.12 | 60.10 | .01 | 4.48 | 7.98 | .140 | .0012 | .320 | 6.28 | .0011 | .0010 | .0005 | .0250 | .002 | .0275 | .0003 | .051 | .0080 |
| 38 | SY2 | 4.29 | 2.70 | 12.10 | 60.62 | .02 | 4.54 | 8.36 | .127 | .0002 | .340 | 6.42 | .0008 | .0036 | .0001 | .0292 | .000 | .0284 | .0006 | .039 | .0086 |
| 39 | UM1 | .08 | 36.05 | 1.00 | 37.60 | 3.53 | .03 | 2.34 | .100 | .3080 | .160 | 19.13 | .0290 | .8300 | .4100 | .0096 | | .0032 | .0000 | | |
| 40 | UM1 | .13 | 35.50 | .93 | 37.31 | 3.56 | .00 | 2.21 | .062 | .2800 | .156 | 19.00 | .0314 | .8362 | .4073 | .0144 | .005 | .0012 | .0000 | .006 | .0029 |
| 41 | UM4 | .45 | 22.50 | 8.98 | 39.35 | .44 | .18 | 6.27 | .350 | 1.7728 | .150 | 14.23 | .0070 | .1900 | .0540 | .0064 | | .0010 | .0000 | .002 | .0014 |
| 42 | UM4 | .45 | 23.50 | 8.64 | 39.94 | .45 | .14 | 6.40 | .331 | 1.7559 | .163 | 14.21 | .0093 | .1988 | .0576 | .0071 | .005 | .0700 | .0700 | .112 | .1000 |
| 43 | VSN | 5.95 | 4.51 | 13.44 | 55.57 | | 8.12 | 4.53 | 1.080 | .0700 | .100 | 4.14 | .0700 | .0800 | .0800 | .0800 | | .0700 | | .108 | |
| 44 | VSN | 6.01 | 4.35 | 13.11 | 55.52 | .05 | 7.96 | 4.47 | 1.014 | .0664 | .104 | 3.92 | .0684 | .0842 | .0777 | .0830 | .009 | .0739 | .0521 | | .1118 |

EXAMPLE 2

Conventional smelter products and intermediate products with higher sulphur and/or metal contents were selected for sample preparation in accordance with the invention. These products and their main constituents are shown in Table 3 below.

TABLE 3

| Sample | Type | Main Constituents |
|---|---|---|
| 1 | Dross smelt slag | Si > 15, Fe > 20, Zn > 5, Pb > 5 |
| 2 | Copper matte | S > 20, Fe > 20, Cu > 40 |
| 3 | White metal | S = 20, Cu > 75 |
| 4 | Clinker | Zn > 70, Pb < 10 |
| 5 | Lead smelt slag | Si > 5, Fe > 10, Zn > 5, Pb > 20 |
| 6 | Copper concentrate | S = 35, Fe = 31, Cu = 25, Zn = 3 |
| 7 | Zinc concentrate | S = 30, Fe = 16, Zn = 45, Pb = 7 |
| 8 | Lead concentrate | S = 18, Fe = 8, Zn = 4, Pb = 65 |
| 9 | Pyrite concentrate | S > 50, Fe > 40 |
| 10 | Roasted goods | S > 15, Fe > 20, Cu > 20, Zn > 5 |
| 11 | Fuming, converter and final slag | Si > 35, Fe > 50 |
| 12 | EGR-dust | S > 5, Fe > 15, Cu > 10, Zn > 20, Pb > 5 |

All samples were examined with X-ray diffraction and all were found to be amorphous, since no crystalline phases were observed in the resultant diffractograms. It should be noted that samples 1-5 above were also prepared in accordance with the so-called LDF-technique and as before mentioned only samples 1 and 5 could be converted into amorphous sample bodies.

One conclusive characteristic of the novel sample preparing technique achieved in accordance with the inventive method is that it affords the following advantages:

The possibility of producing amorphous, glassy sample bodies of all relevant inorganic products that can occur in conjunction with, e.g., prospecting, inorganic process industries and environmental care projects;

The possibility of combining the analysis of sulphur, rock formers, metals and trace substances with the aid of a single sample body;

X-ray-spectral or optical-spectral methods can be applied with all relevant products;

Large sample quantities can be used in comparison with other, known methods applied in the analysis of comparable materials (much greater accuracy); and The analyses can be carried out in standard, wet-chemical laboratories with the minimum of equipment.

We claim:

1. A method of preparing amorphous sample bodies for optical spectral analysis and x-ray spectral analysis, comprising; fusing an analysis sample together with a flux, and adding finely-divided $SiO_2$ in an amount corresponding to 1–100% by weight of said analysis sample prior to the fusion process.

2. A method according to claim 1, further comprising; adding an oxidation agent in a predetermined quantity in order to oxidize sulphur and other oxidizable elements in said analysis sample, said oxidation agent being added in an amount corresponding to between about 50% and about 200% by weight of the analysis sample.

3. A method according to claim 2, further comprising; subjecting said analysis sample and its additives, said flux, said finely-divided $SiO_2$ and said oxidation agent to an oxidizing treatment process at elevated temperature prior to the fusion process.

4. A method according to claim 3, wherein said oxidation agent is lithium nitrate.

5. A method according to claim 4, wherein said fusion process is effected in a platina crucible.

6. A method according to claim 5, wherein said fusion process is effected in an electrical resistance furnace at a temperature of about 1200° C.

7. A method according to claim 6, wherein said fusion process is effected in two separate periods with intermediate agitation of the fused material.

8. A method according to claim 2, wherein said oxidation agent is lithium nitrate.

9. A method according to claim 1, further comprising subjecting said analysis sample and its additives, said flux and said finely-divided $SiO_2$, to an oxidizing treatment process at elevated temperature prior to the fusion process.

10. A method according to claim 1, wherein said fusion process is effected in a platina crucible.

11. A method according to claim 1, wherein said fusion process is effected in an electrical resistance furnace at a temperature of about 1200° C.

12. A method according to claim 12, wherein said fusion process is effected in two separate periods with intermediate agitation of the fused material.

* * * * *